US011040086B2

(12) United States Patent
Zhang et al.

(10) Patent No.: US 11,040,086 B2
(45) Date of Patent: Jun. 22, 2021

(54) ACTIVE PEPTIDE FOR ENHANCING THE PHAGOCYTIC FUNCTIONS OF RETINAL PIGMENT EPITHELIUM AND A USE THEREOF

(71) Applicant: Beijing Tongren Hospital, Capital Medical University, Beijing (CN)

(72) Inventors: Jingxue Zhang, Beijing (CN); Shen Wu, Beijing (CN); Ningli Wang, Beijing (CN)

(73) Assignee: Beijing Tongren Hospital, Capital Medical University, Beijing (CN)

( * ) Notice: Subject to any disclaimer, the term of this patent is extended or adjusted under 35 U.S.C. 154(b) by 0 days.

(21) Appl. No.: 16/730,251

(22) Filed: Dec. 30, 2019

(65) Prior Publication Data

US 2020/0390853 A1 Dec. 17, 2020

(30) Foreign Application Priority Data

Jun. 14, 2019 (CN) ........................ 201910514282.X

(51) Int. Cl.
*A61K 38/45* (2006.01)
*A61P 27/02* (2006.01)
*A61K 38/17* (2006.01)

(52) U.S. Cl.
CPC .......... *A61K 38/1709* (2013.01); *A61K 38/45* (2013.01); *A61P 27/02* (2018.01)

(58) Field of Classification Search
CPC ...... A61K 38/1709; A61K 38/45; A61P 27/02
See application file for complete search history.

(56) References Cited

U.S. PATENT DOCUMENTS 5,538,861 A * 7/1996 Schneider ............ C07K 14/475 435/252.3
6,211,142 B1 * 4/2001 Hammonds .......... C07K 14/745 514/6.5

OTHER PUBLICATIONS

Sayama et al., "UNC569-induced Morphological Changes in Pigment Epithelia and Photoreceptor Cells in the Retina through MerTK inhibition in Mice," Toxicology Pathology, 2018, 46(2): 193-201. (Year: 2018).*

* cited by examiner

*Primary Examiner* — Julie Ha
(74) *Attorney, Agent, or Firm* — Mintz Levin Cohn Ferris Glovsky and Popeo, P.C.

(57) ABSTRACT

An active peptide for enhancing the phagocytic functions of retinal pigment epithelium and a use thereof, which belongs to the technical field of preparing drugs for treating retinal neurodegenerative diseases, are described. The amino acid sequence of the active peptide for enhancing the phagocytic functions of retinal pigment epithelium described in the disclosure was as shown in SEQ ID NO.1. The active peptide of the present invention has biological characteristics similar to those of Gas6 full-length proteins, with an effect of enhancing the phagocytic functions of retinal pigment epithelium.

3 Claims, 3 Drawing Sheets
(3 of 3 Drawing Sheet(s) Filed in Color)

Specification includes a Sequence Listing.

SEQUENCE LISTING

```
<160> NUMBER OF SEQ ID NOS: 2

<210> SEQ ID NO 1
<211> LENGTH: 561
<212> TYPE: PRT
<213> ORGANISM: artificial sequence
<220> FEATURE:
<223> OTHER INFORMATION: the amino acid sequence of the active peptide

<400> SEQUENCE: 1

Asp Gln Cys Thr Pro Asn Pro Cys Asp Arg Lys Gly Thr Gln Ala Cys
1               5                   10                  15

Gln Asp Leu Met Gly Asn Phe Phe Cys Leu Cys Lys Ala Gly Trp Gly
            20                  25                  30

Gly Arg Leu Cys Asp Lys Asp Val Asn Glu Cys Ser Gln Glu Asn Gly
        35                  40                  45

Gly Cys Leu Gln Ile Cys His Asn Lys Pro Gly Ser Phe His Cys Ser
    50                  55                  60
```

-continued

```
Cys His Ser Gly Phe Glu Leu Ser Ser Asp Gly Arg Thr Cys Gln Asp
65                  70                  75                  80

Ile Asp Glu Cys Ala Asp Ser Glu Ala Cys Gly Glu Ala Arg Cys Lys
                85                  90                  95

Asn Leu Pro Gly Ser Tyr Ser Cys Leu Cys Asp Glu Gly Phe Ala Tyr
            100                 105                 110

Ser Ser Gln Glu Lys Ala Cys Arg Asp Val Asp Glu Cys Leu Gln Gly
        115                 120                 125

Arg Cys Glu Gln Val Cys Val Asn Ser Pro Gly Ser Tyr Thr Cys His
    130                 135                 140

Cys Asp Gly Arg Gly Gly Leu Lys Leu Ser Gln Asp Met Asp Thr Cys
145                 150                 155                 160

Glu Asp Ile Leu Pro Cys Val Pro Phe Ser Val Ala Lys Ser Val Lys
                165                 170                 175

Ser Leu Tyr Leu Gly Arg Met Phe Ser Gly Thr Pro Val Ile Arg Leu
            180                 185                 190

Arg Phe Lys Arg Leu Gln Pro Thr Arg Leu Val Ala Glu Phe Asp Phe
        195                 200                 205

Arg Thr Phe Asp Pro Glu Gly Ile Leu Leu Phe Ala Gly Gly His Gln
    210                 215                 220

Asp Ser Thr Trp Ile Val Leu Ala Leu Arg Ala Gly Arg Leu Glu Leu
225                 230                 235                 240

Gln Leu Arg Tyr Asn Gly Val Gly Arg Val Thr Ser Ser Gly Pro Val
                245                 250                 255

Ile Asn His Gly Met Trp Gln Thr Ile Ser Val Glu Glu Leu Ala Arg
            260                 265                 270

Asn Leu Val Ile Lys Val Asn Arg Asp Ala Val Met Lys Ile Ala Val
        275                 280                 285

Ala Gly Asp Leu Phe Gln Pro Glu Arg Gly Leu Tyr His Leu Asn Leu
    290                 295                 300

Thr Val Gly Gly Ile Pro Phe His Glu Lys Asp Leu Val Gln Pro Ile
305                 310                 315                 320

Asn Pro Arg Leu Asp Gly Cys Met Arg Ser Trp Asn Trp Leu Asn Gly
                325                 330                 335

Glu Asp Thr Thr Ile Gln Glu Thr Val Lys Val Asn Thr Arg Met Gln
            340                 345                 350

Cys Phe Ser Val Thr Glu Arg Gly Ser Phe Tyr Pro Gly Ser Gly Phe
        355                 360                 365

Ala Phe Tyr Ser Leu Asp Tyr Met Arg Thr Pro Leu Asp Val Gly Thr
    370                 375                 380

Glu Ser Thr Trp Glu Val Glu Val Val Ala His Ile Arg Pro Ala Ala
385                 390                 395                 400

Asp Thr Gly Val Leu Phe Ala Leu Trp Ala Pro Asp Leu Arg Ala Val
                405                 410                 415

Pro Leu Ser Val Ala Leu Val Asp Tyr His Ser Thr Lys Lys Leu Lys
            420                 425                 430

Lys Gln Leu Val Val Leu Ala Val Glu His Thr Ala Leu Ala Leu Met
        435                 440                 445

Glu Ile Lys Val Cys Asp Gly Gln Glu His Val Val Thr Val Ser Leu
    450                 455                 460

Arg Asp Gly Glu Ala Thr Leu Glu Val Asp Gly Thr Arg Gly Gln Ser
465                 470                 475                 480
```

-continued

```
Glu Val Ser Ala Ala Gln Leu Gln Glu Arg Leu Ala Val Leu Glu Arg
                485                 490                 495

His Leu Arg Ser Pro Val Leu Thr Phe Ala Gly Gly Leu Pro Asp Val
            500                 505                 510

Pro Val Thr Ser Ala Pro Val Thr Ala Phe Tyr Arg Gly Cys Met Thr
        515                 520                 525

Leu Glu Val Asn Arg Arg Leu Leu Asp Leu Asp Glu Ala Ala Tyr Lys
    530                 535                 540

His Ser Asp Ile Thr Ala His Ser Cys Pro Pro Val Glu Pro Ala Ala
545                 550                 555                 560

Ala


<210> SEQ ID NO 2
<211> LENGTH: 1683
<212> TYPE: DNA
<213> ORGANISM: artificial sequence
<220> FEATURE:
<223> OTHER INFORMATION: the nucleotide sequence of the active peptide

<400> SEQUENCE: 2

gaccagtgca cgcccaaccc ctgcgatagg aaggggaccc aagcctgcca ggacctcatg     60

ggcaacttct tctgcctgtg taaagctggc tggggggggcc ggctctgcga caaagatgtc   120

aacgaatgca gccaggagaa cggggggctgc ctccagatct gccacaacaa gccgggtagc   180

ttccactgtt cctgccacag cggcttcgag ctctcctctg atggcaggac ctgccaagac   240

atagacgagt gcgcagactc ggaggcctgc ggggaggcgc gctgcaagaa cctgcccggc   300

tcctactcct gcctctgtga cgagggcttt gcgtacagct cccaggagaa ggcttgccga   360

gatgtggacg agtgtctgca gggccgctgt gagcaggtct gcgtgaactc cccagggagc   420

tacacctgcc actgtgacgg gcgtgggggc ctcaagctgt cccaggacat ggacacctgt   480

gaggacatct tgccgtgcgt gcccttcagc gtggccaaga gtgtgaagtc cttgtacctg   540

ggccggatgt tcagtgggac cccccgtgatc cgactgcgct tcaagaggct gcagcccacc   600

aggctggtag ctgagtttga cttccggacc tttgaccccg agggcatcct cctctttgcc   660

ggaggccacc aggacagcac ctggatcgtg ctggccctga gagccggccg gctggagctg   720

cagctgcgct acaacggtgt cggccgtgtc accagcagcg gcccggtcat caaccatggc   780

atgtggcaga caatctctgt tgaggagctg gcgcggaatc tggtcatcaa ggtcaacagg   840

gatgctgtca tgaaaatcgc ggtggccggg gacttgttcc aaccggagcg aggactgtat   900

catctgaacc tgaccgtggg aggtattccc ttccatgaga aggacctcgt gcagcctata   960

aaccctcgtc tggatggctg catgaggagc tggaactggc tgaacggaga agacaccacc  1020

atccaggaaa cggtgaaagt gaacacgagg atgcagtgct tctcggtgac ggagagaggc  1080

tctttctacc ccgggagcgg cttcgccttc tacagcctgg actacatgcg gacccctctg  1140

gacgtcggga ctgaatcaac ctgggaagta gaagtcgtgg ctcacatccg cccagccgca  1200

gacacaggcg tgctgtttgc gctctgggcc cccgacctcc gtgccgtgcc tctctctgtg  1260

gcactggtag actatcactc cacgaagaaa ctcaagaagc agctggtggt cctggccgtg  1320

gagcatacgg ccttggccct aatggagatc aaggtctgcg acggccaaga gcacgtggtc  1380

accgtctcgc tgagggacgg tgaggccacc ctggaggtgg acggcaccag gggccagagc  1440

gaggtgagcg ccgcgcagct gcaggagagg ctggccgtgc tcgagaggca cctgcggagc  1500

cccgtgctca cctttgctgg cggcctgcca gatgtgccgg tgacttcagc gccagtcacc  1560
```

-continued

```
gcgttctacc gcggctgcat gacactggag gtcaaccgga ggctgctgga cctggacgag   1620

gcggcgtaca agcacagcga catcacggcc cactcctgcc cccccgtgga gcccgccgca   1680

gcc                                                                 1683
```

ACTIVE PEPTIDE FOR ENHANCING THE PHAGOCYTIC FUNCTIONS OF RETINAL PIGMENT EPITHELIUM AND A USE THEREOF

CROSS REFERENCE TO RELATED APPLICATIONS

The present application claims priority to Chinese Patent Appl. No. 201910514282.X to Zhang et al., filed Jun. 14, 2019 and entitled "An Active Peptide for Enhancing the Phagocytic Functions of Retinal Pigment Epithelium and a Use Thereof", and incorporates its disclosure herein by reference in its entirety.

TECHNICAL FIELD

The disclosure relates to the technical field of preparing drugs for treating retinal neurodegenerative diseases, specifically relates to an active peptide for enhancing the phagocytic functions of retinal pigment epithelium and a use thereof.

BACKGROUND

With inflammatory eye diseases and optically related eye diseases gradually being controlled effectively, retinal neurodegenerative diseases have become the primary cause of irreversible blindness for the present world, affecting the vision health of tens of millions of people, such as Retinitis Pigmentosa (RP), Age-related Macular Degeneration (AMD) and Leber Congenital Amaurosis (LCA), etc.

There have been no effective treatments for such diseases currently, which affect the vision and living quality of tens of millions of people, being the main factor of causing vision disabilities and blindness. Therefore, it is an urgent need to explore novel and effective treatments for reconstructing the structures and restoring the functions of visual systems. Among the above diseases, retinal pigment epitheliums (RPEs) are the main initial damaging factors. RPEs are monolayer cells between neural retina and Bruch's membrane, with functions of phagocytosing the photoreceptor cell outer segments, secreting trophic factors, participating in visual cycle and metabolism and forming blood-retina barrier, which are very important for maintaining normal physiological functions of retina. Damages on the phagocytic functions of retinal pigment epitheliums would cause the developments of retinal degenerative diseases such as AMD, RP and LCA, etc.

Gas6 proteins have therapeutic potentials of improving retina microenvironments, and promoting gene therapies or cell therapies to work. However, there remained the following problems of Gas6 proteins in clinical transformation applications: single injection intervention caused short biological effects, while repeated sub-retinal injections would lead to numerous complications as well as compliance issues of patients and the like. Therefore, it became a key point in the field that how to achieve effective clinical intervention of Gas6 proteins, and to play long-term roles in retina microenvironments, thus upregulating the functions of RPE phagocytosis, and delaying damages from diseases.

In recent years, sustained-release drug delivery technologies and nanoscale envelope technologies provided good technical routes for sustained-release delivery of proteins, while macromolecular substances such as proteins were highly susceptible to physical and chemical factors during the production processes and thus being inactivated, and the effective clinical intervention could not be realized with Gas6 proteins.

SUMMARY

The object of the present invention is to provide an active peptide for enhancing the phagocytic functions of retinal pigment epithelium and a use thereof. The active peptide of the present invention has biological characteristics similar to those of Gas6 full-length proteins, with small molecular weight and not prone to be inactivated, and has an effect of enhancing the phagocytic functions of retinal pigment epithelium.

The present invention provides an active peptide for enhancing the phagocytic functions of retinal pigment epithelium, the amino acid sequence of the active peptide is as shown in SEQ ID NO.1.

Preferably, the nucleotide sequence of the active peptide is as shown in SEQ ID NO.2.

The present invention further provides a drug for enhancing the phagocytic functions of retinal pigment epithelium, the drug includes the active peptide described above.

Preferably, the drug further includes MerTK.

The present invention further provides a use of the above active peptide in preparing drugs for preventing or treating degenerative diseases of retina.

The present invention provides an active peptide for enhancing the phagocytic functions of retinal pigment epithelium. The active peptide of the present invention has biological characteristics similar to those of Gas6 full-length proteins, with an effect of enhancing the phagocytic functions of retinal pigment epithelium; and at the same time, has better biological stabilities due to its small molecular weight, being more suitable for the production of coatings for sustained-release delivery materials; suitable for long-term sustained-release actions in treating degenerative diseases of retina, improving the pathological microenvironments, and assisting cell therapies or gene therapies to provide therapeutic effects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other aspects will now be described in detail with reference to the following drawings.

DESCRIPTION OF THE EMBODIMENTS

Figures 1, 2:
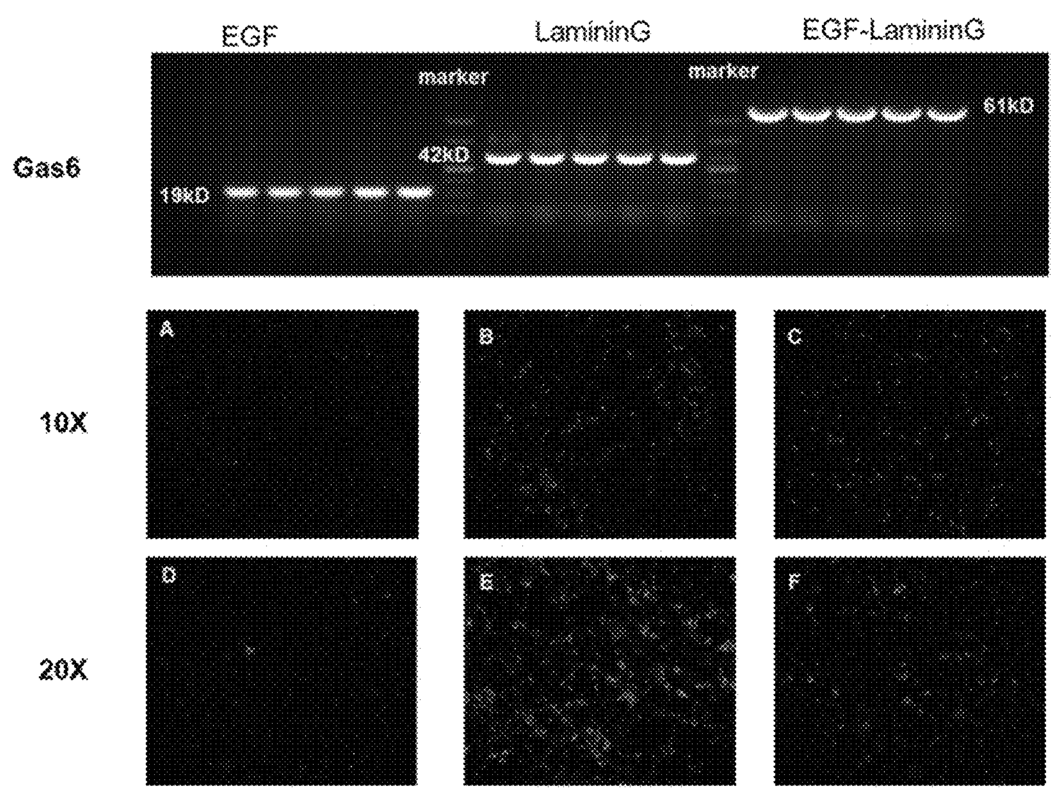
FIG. 1 is the tertiary structure diagram of the active peptide for enhancing the phagocytic functions of retinal pigment epithelium provided in the present invention.
FIG. 2 is the construction and expression results of the active peptide with different functional fragments of Gas6 provided in Embodiment 1 of the present invention.

The present invention provides an active peptide for enhancing the phagocytic functions of retinal pigment epithelium, the amino acid sequence of the active peptide is as shown in SEQ ID NO.1: dqc tpnpcdrkgt qacqdlmgnf fcickagwgg rlcdkdvnec sqenggclqi chnkpgsfhc schsgfelss dgrtcqdide cadseacgea rcknlpgsys cicdegfays sqekacrdvd eclqgrceqv cvnspgsytc hcdgrgglkl sqdmdtcedi lpcvpfsvak svkslylgrm fsgtpvirlr fkrlqptrlv aefdfrtfdp egillfaggh qdstwivlal ragrlelqlr yngvgrvtss gpvinhgmwq tisveelarn lvikvnrdav mkiavagdlf qperglyhln ltvggipfhe kdlvqpinpr ldgcmrswnw lngedttiqe tvkvntrmqc fsvtergsfy pgsgfafysl dymrtpldvg testwevevv ahirpaadtg vlfalwapdl ravplsvalv dyhstkklkk qlvvlaveht alalmeikvc dgqehvvtvs lrdgeatlev dgtrgqsevs aaqlqerlav lerhlrspvl tfagglpdvp vtsapvtafy rgcmtlevnr rlldldeaay khsditahsc ppvepaaa. The tertiary structure diagram of the active peptide for enhancing the phagocytic functions of retinal pigment epithelium is as shown in FIG. 1.

There remained the following problems of Gas6 proteins in clinical transformation applications: single injection intervention caused short biological effects, while repeated subretinal injections would lead to numerous complications as well as compliance issues of patients and the like; due to that Gas6 proteins belong to protein macromolecules with fragile and variable high-level structures, they are prone to degenerate and be inactivated during the coating process of sustained-release materials, thus being not applicable any more, Gas6 proteins are not capable of achieving effective clinical intervention, and playing long-term roles in retina microenvironments, thus upregulating the functions of RPE phagocytosis, and delaying damages from diseases.

In the present invention, segmented cloning was conducted according to the functional domain of Gas6 protein, wherein the sequence of EGF-LamininG functional domain is the primary active peptide sequence (named as Gas6-LamininG active peptide, G3, that is the active peptide of the present invention), the Gas6-LamininG active peptide, compared with Gas6 full-length proteins, has low molecular weight, while with similar effects, both being capable of significantly upregulating the Akt phosphorylation level, promoting the effect of the phagocytic function of RPE cells, and assisting to delay the development of degenerative diseases of retina. During the preparation of sustained-release formulations, the Gas6-LamininG active peptide of the present invention may maintain the nature forms and biological activities of proteins, and enhance pharmacodynamic properties and ease of administration.

The active peptide of the invention is obtained by constructing a system of in vitro expression and purification for Gas6 functional active peptides with relative small molecular weights in the present invention. There were no special limitations on the methods of in vitro expression and purification, as long as employing the conventional system of protein expression and purification which is well known to persons skilled in the art.

In the present invention, the nucleotide sequence of the active peptide is as shown in SEQ ID NO.2: GACCAGTGCA CGCCCAACCC CTGCGATAGG AAGGGGACCC AAGCCTGCCA GGACCTCATG GGCAACTTCT TCTGCCTGTG TAAAGCTGGC TGGGGGGGCC GGCTCTGCGA CAAAGATGTC AACGAATGCA GCCAGGAGAA CGGGGGCTGC CTCCAGATCT GCCACAACAA GCCGGGTAGC TTCCACTGTT CCTGCCACAG CGGCTTCGAG CTCTCCTCTG ATGGCAGGAC CTGCCAAGAC ATAGACGAGT GCGCAGACTC GGAGGCCTGC GGGGAGGCGC GCTGCAAGAA CCTGCCCGGC TCCTACTCCT GCCTCTGTGA CGAGGGCTTT GCGTACAGCT CCCAGGAGAA GGCTTGCCGA GATGTGGACG AGTGTCTGCA GGGCCGCTGT GAGCAGGTCT GCGTGAACTC CCCAGGGAGC TACACCTGCC ACTGTGACGG GCGTGGGGGC CTCAAGCTGT CCCAGGACAT GGACACCTGT GAGGACATCT TGCCGTGCGT GCCCTTCAGC GTGGCCAAGA GTGTGAAGTC CTTGTACCTG GGCCGGATGT TCAGTGGGAC CCCCGTGATC CGACTGCGCT TCAAGAGGCT GCAGCCCACC AGGCTGGTAG CTGAGTTTGA CTTCCGGACC TTTGACCCCG AGGGCATCCT CCTCTTTGCC GGAGGCCACC AGGACAGCAC CTGGATCGTG CTGGCCCTGA GAGCCGGCCG GCTGGAGCTG CAGCTGCGCT ACAACGGTGT CGGCCGTGTC ACCAGCAGCG GCCCGGTCAT CAACCATGGC ATGTGGCAGA CAATCTCTGT TGAGGAGCTG GCGCGGAATC TGGTCATCAA GGTCAACAGG GATGCTGTCA TGAAAATCGC GGTGGCCGGG GACTTGTTCC AACCGGAGCG AGGACTGTAT CATCTGAACC TGACCGTGGG AGGTATTCCC TTCCATGAGA AGGACCTCGT GCAGCCTATA AACCCTCGTC TGGATGGCTG CATGAGGAGC TGGAACTGGC TGAACGGAGA AGACACCACC ATCCAGGAAA CGGTGAAAGT GAACACGAGG ATGCAGTGCT TCTCGGTGAC GGAGAGAGGC TCTTTCTACC CCGGGAGCGG CTTCGCCTTC TACAGCCTGG ACTACATGCG GACCCCTCTG GACGTCGGGA CTGAATCAAC CTGGGAAGTA GAAGTCGTGG CTCACATCCG CCCAGCCGCA GACACAGGCG TGCTGTTTGC GCTCTGGGCC CCCGACCTCC GTGCCGTGCC TCTCTCTGTG GCACTGGTAG ACTATCACTC CACGAAGAAA CTCAAGAAGC AGCTGGTGGT CCTGGCCGTG GAGCATACGG CCTTGGCCCT AATGGAGATC AAGGTCTGCG ACGGCCAAGA GCACGTGGTC ACCGTCTCGC TGAGGGACGG TGAGGCCACC CTGGAGGTGG ACGGCACCAG GGGCCAGAGC GAGGTGAGCG CCGCGCAGCT GCAGGAGAGG CTGGCCGTGC TCGAGAGGCA CCTGCGGAGC CCCGTGCTCA CCTTTGCTGG CGGCCTGCCA GATGTGCCGG TGACTTCAGC GCCAGTCACC GCGTTCTACC GCGGCTGCAT GACACTGGAG GTCAACCGGA GGCTGCTGGA CCTGGACGAG GCGGCGTACA AGC ACAGCGA CATCACGGCC CACTCCTGCC CCCCCGTGGA GCCCGCCGCAGCC.

The present invention further provides a drug for enhancing the phagocytic functions of retinal pigment epithelium, the drug includes the active peptide described above.

In the present invention, the drug preferably further includes MerTK. The drug of the invention improves diseases by combining the active peptide with mertk gene therapies, or combining with cell transplantation alternative therapies, and further synergistically promoting the phagocytic functions of retinal pigment epithelium.

The present invention further provides a use of the active peptide described above in preparing drugs for preventing or treating degenerative disease of retina.

The active peptide for enhancing the phagocytic functions of retinal pigment epithelium and a use thereof in the present invention would be further illustrated in detail in conjunction with the following specific embodiments, the technical schemes of the present invention include, but not limited to, the following embodiments.

Embodiment 1

Figure 3:
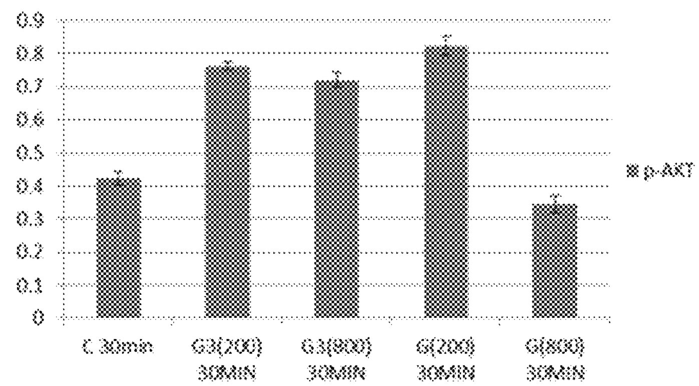
FIG. 3 is the results of changes in AKT phosphorylation level after treatment of RPE cells with the active peptide with different fragments of Gas6 provided in Embodiment 1 of the present invention.

Segmented cloning was conducted according to the functional domain of Gas6 protein, wherein the sequence of EGF-LamininG functional domain is the primary active peptide sequence (G3, named as Gas6-LamininG active peptide). Through constructing eukaryotic and prokaryotic expression systems for sequences of each functional domain of Gas6 gene, in vitro expression and purification were conducted (the construction expression results of the active peptide with different functional fragments of Gas6 were as shown in FIG. 2, wherein, A: expression of the constructed EGF plasmid in the eukaryotic cells, objective lens of 10 times; B: expression of the constructed LamininG plasmid in the eukaryotic cells, objective lens of 10 times; C: expression of the constructed EGF-LamininG plasmid in the eukaryotic cells, objective lens of 10 times; D-F: observation from the corresponding objective lens of 20 times). As can be seen from FIG. 2, the several short peptides constructed could all be expressed normally in cells. RPE cells cultivated in vitro were treated with the Gas6-LamininG active peptide obtained from purification at different concentrations (200 ng/ml, 800 ng/ml), detecting the AKT phosphorylation level downstream of MerTK (indicating the initiation of cytophagocytic pathway), with the results showing that the Gas6-LamininG active peptide has similar effects to those of Gas6 full-length proteins, both being capable of significantly upregulating Akt phosphorylation levels (the results of changes in AKT phosphorylation level after treatment of RPE cells with the active peptide with different fragments of Gas6 were as shown in FIG. 3, wherein, horizontal ordinate: C30 min: the blank control group (treatment in normal medium for 30 minutes) ; G3(200)30 min : the group of cells by treatment with a medium containing 200 ng/ml of Gas6-LamininG active peptide for 30 minutes; G3(800)30 min: the group of cells by treatment with a medium containing 800 ng/ml of Gas6-LamininG active peptide for 30 minutes; G (200)30 min: the group of cells by treatment with a medium containing 200 ng/ml of Gas6 full-length proteins for 30 minutes; G 2(800) 30 min: the group of cells by treatment with a medium containing 800 ng/ml of Gas6 full-length proteins for 30 minutes; vertical ordinate: results of Western blotting detection, the relative gray value of pAKT/GAPDH (internal reference)).

Figure 4:
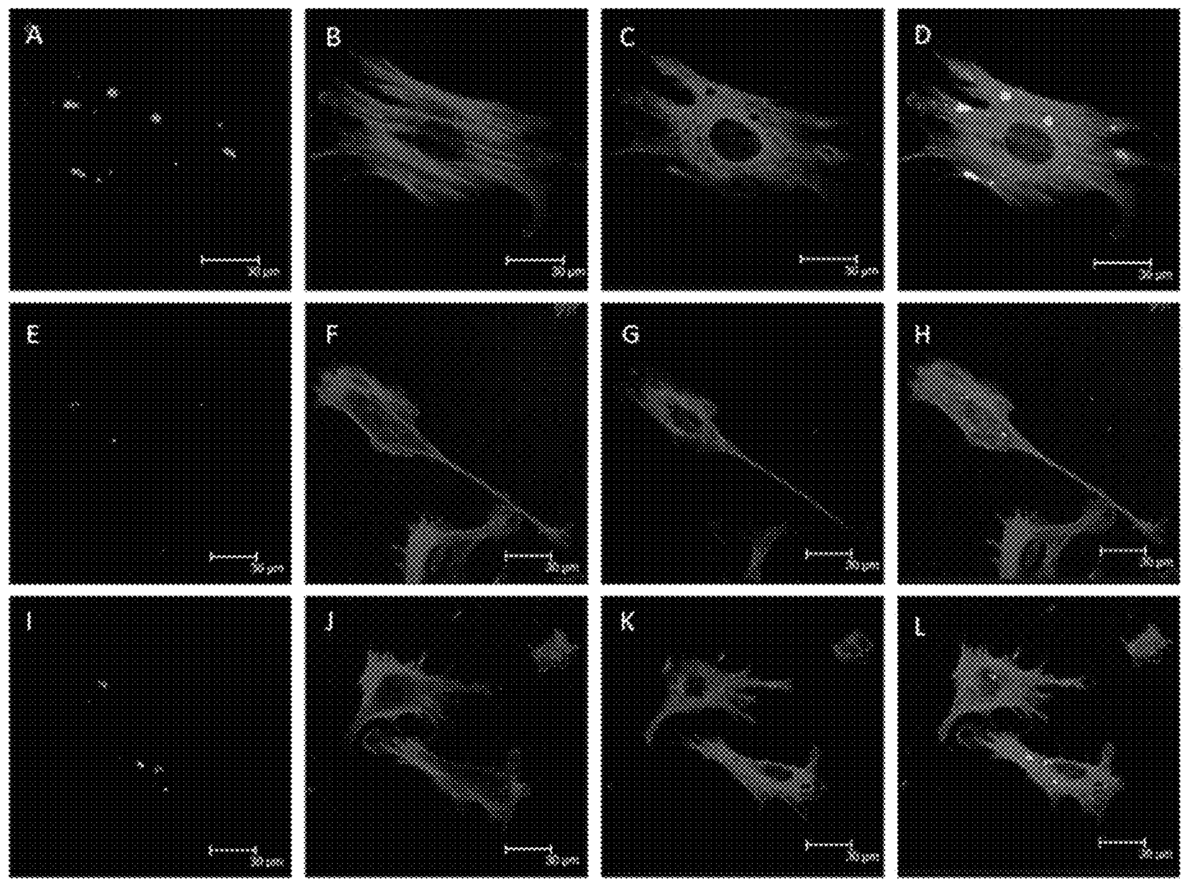
FIG. 4 is the laser confocal results after 3 h of RPE phagocytosis provided in Embodiment 1 of the present invention.

In the model of in vitro RPE phagocytosis, it can be seen that after different interventions, the RPE phagocytosis capacity of the control group was stronger, taking up more and complete disc membranes, the contents of disc membranes taken up by MerTK/Gas6-LamininG active peptide in conjunction with the intervention group were less than that of the wild-type control group, while more than that of the Mertk single intervention group, with significant statistical difference between groups ($p<0.05$)(the laser confocal results after 3 h of RPE phagocytosis were as shown in FIG. 4, wherein, A-D: the control group, E-H: the mertk intervention group, I-L: the mertk+Gas6-LamininG active peptide group, A, E, I in green: disc membrane-FITC, B, F, J in red: actin, C, G, K in purple: tublin, D, H, L in blue: DAPI.bar=30 um). It was demonstrated from the results that: the Gas6-LamininG active peptide has the features of small molecular weight and biological stability, and has biological characteristics similar to those of Gas6 full-length proteins, with an effect of enhancing the phagocytic functions of retinal pigment epithelium.

Figure 5:
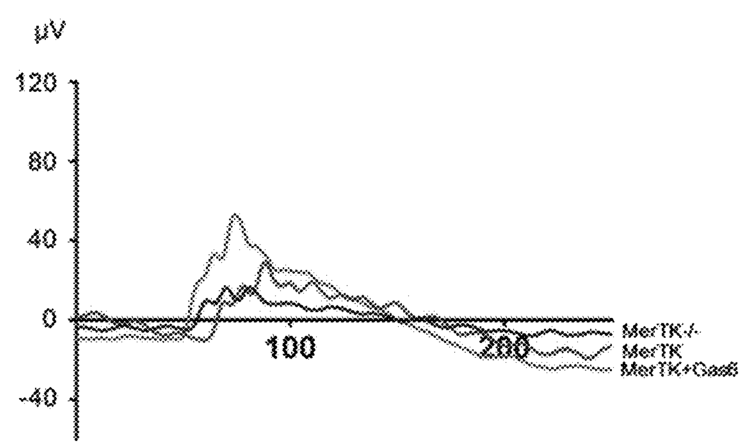
FIG. 5 is the b wave response results of ERG after different interventions on $Mer^{-/-}$ mice provided in Embodiment 1 of the present invention.

By continuously selecting P17 $Mer^{-/-}$ mice as the experimental animals, the exogenous AAV2-MerTK/Gas6 LamininG active peptide was implanted into the sub-retinal space (AAV2-MerTK single intervention group, MerTK/Gas6 LamininG active peptide combined intervention group and the blank control group). 8 weeks after the operation, each group was compared by detecting the improvement of visual function with visual electrophysiology, to analyze the variation differences. It was shown from the results of electrophysiological detection, for b waves representing retinal rod cells and RPE functions (dark adaptation 0.01ERG), the amplitudes in MerTK/Gas6 LamininG active peptide combined transplantation group and AAV2-Mertk single transplantation group were both greater than that of the control group significantly; and the enhancement in the combined intervention group was the most significant ($p<0.01$, FIG. 5 is the b wave responses (dark adaptation 0.01ERG) of ERG after different interventions on $Mer^{-/-}$ mice). It was confirmed that the MerTK/Gas6 LamininG active peptide combined intervention could enhance the visual function of $Mer^{-/-}$ mice.

The above descriptions were only the preferred detailed description of the invention, it should be noted to persons with ordinary skills in the art that several improvements and modifications could be made without deviating from the principle of the invention, which also should be considered in the scope of the invention.

What is claimed:

1. An active peptide for enhancing the phagocytic functions of retinal pigment epithelium, wherein the amino acid sequence of the active peptide consists of SEQ ID NO: 1.

2. A drug for enhancing the phagocytic functions of retinal pigment epithelium, wherein the drug comprises the active peptide of claim 1.

3. The drug according to claim 2, wherein the drug further comprises c-mer proto-oncogene tyrosine kinase.

* * * * *